United States Patent
Noce et al.

(10) Patent No.: US 9,968,269 B1
(45) Date of Patent: May 15, 2018

(54) WIRELESS DISPOSABLE ANGIOPLASTY TRANSDUCER MANIFOLD

(71) Applicants: Louis O. Noce, Sanford, FL (US);
Alisa A. Noce, Sanford, FL (US)

(72) Inventors: Louis O. Noce, Sanford, FL (US);
Alisa A. Noce, Sanford, FL (US)

(*) Notice: Subject to any disclaimer, the term of this patent is extended or adjusted under 35 U.S.C. 154(b) by 789 days.

(21) Appl. No.: 14/016,884

(22) Filed: Sep. 3, 2013

Related U.S. Application Data

(60) Provisional application No. 61/695,415, filed on Aug. 31, 2012.

(51) Int. Cl.
*A61B 5/02* (2006.01)
*A61B 5/0215* (2006.01)
*A61B 5/00* (2006.01)

(52) U.S. Cl.
CPC .......... *A61B 5/0215* (2013.01); *A61B 5/0004* (2013.01); *A61B 5/742* (2013.01)

(58) Field of Classification Search
None
See application file for complete search history.

(56) References Cited

U.S. PATENT DOCUMENTS

| | | | |
|---|---|---|---|
| 3,831,588 A | 8/1974 | Rindner | |
| 4,114,187 A * | 9/1978 | Uke | F21L 4/08 200/60 |
| 4,960,127 A * | 10/1990 | Noce | A61B 5/0215 600/488 |
| 5,318,533 A * | 6/1994 | Adams | A61M 25/1018 128/903 |
| 5,810,738 A | 9/1998 | Thomas, II | |
| 6,139,503 A | 10/2000 | Müller | |
| 6,511,434 B1 * | 1/2003 | Haytman | A61B 5/0215 600/479 |
| 7,347,822 B2 | 3/2008 | Brockway et al. | |
| 7,510,533 B2 | 3/2009 | Mauge et al. | |
| 7,959,579 B2 | 6/2011 | Dijkman | |
| 7,976,475 B2 | 7/2011 | Dijkman | |
| 2004/0193058 A1 | 9/2004 | Montegrande et al. | |
| 2006/0171145 A1 * | 8/2006 | Ford | F21L 4/027 362/200 |

(Continued)

FOREIGN PATENT DOCUMENTS

DE EP0710490 5/1996

*Primary Examiner* — Michael R Bloch
(74) *Attorney, Agent, or Firm* — H. John Rizvi; Gold & Rizvi, P.A.

(57) ABSTRACT

A wireless disposable angioplasty transducer manifold is disclosed. The wireless disposable angioplasty transducer manifold includes am elongated manifold frame and a hollow elongated tubular manifold disposed within the frame. The hollow elongated tubular manifold has an inlet end for receiving fluid directly from a patient, an outlet end for returning the fluid to the patient, and a passageway extending between the inlet and outlet ends. The transducer manifold also includes at least one valve port and at least one sensing port provided on the tubular manifold, the sensing port having a pressure sensing transducer within a housing formed in the sensing port. A Radio Frequency (RF) or Infra-red (IR) transmitter and battery electrically coupled to the pressure sensing transducer allow for pressure signals to be transmitted wirelessly to remotely located monitoring equipment.

10 Claims, 5 Drawing Sheets

(56) References Cited

U.S. PATENT DOCUMENTS

| | | |
|---|---|---|
| 2007/0112274 A1 | 5/2007 | Heitzmann et al. |
| 2009/0069714 A1 | 3/2009 | Eichmann et al. |
| 2009/0124880 A1* | 5/2009 | Smith .................. A61B 5/0215 600/373 |
| 2012/0226148 A1* | 9/2012 | Jaggi ........................ A61B 5/06 600/424 |

* cited by examiner

WIRELESS DISPOSABLE ANGIOPLASTY TRANSDUCER MANIFOLD

CROSS-REFERENCE TO RELATED APPLICATION

This Non-Provisional Utility application claims the benefit of U.S. Provisional Patent Application Ser. No. 61/695,415, filed on Aug. 31, 2012, which is incorporated herein in its entirety. The actual one-year anniversary falls on a Saturday and the following Monday is a federal holiday (Labor Day). Therefore, Applicant is afforded until Tuesday, Sep. 3, 2013 to file this Non-Provisional Utility application to maintain co-pendency.

FIELD OF THE INVENTION

This invention relates generally to angioplasty pressure sensing in medical applications and, more specifically, to an improved method and apparatus for pressure sensing and monitoring during an angioplasty or angiographic procedure utilizing wireless technology.

BACKGROUND OF THE INVENTION

In conventional angioplasty pressure sensing and monitoring systems, a catheter from the heart or other location is connected to a tubular manifold and frame assembly, which is provided with one or more valve ports. Flexible plastic tubing extends from the manifold ports of the assembly (which is typically attached to the patient's arm, chest, etc.) to one or more pressure sensor and monitoring devices. Each pressure sensor includes a transducer dome and transducer, typically mounted on a vertical post located about six feet away from the patient. In this arrangement, blood passing into and/or through the manifold may be periodically diverted via conventional petcock type valves through a pressure monitoring tube connected between one of the manifold ports and post-mounted pressure sensor.

The prior art pressure sensors have multiple wires leading from the pressure sensors to a blood pressure recorder or other equipment. The use of wiring for electrically connecting the pressure sensors to a blood pressure recorder has proved less than optimal. When a patient is not present, the wires may become unplugged, causing the burden of having to plug the wires back into the correct ports on the pressure sensors. When a patient is present, the wires add to clutter in the patient area, which generally has other instrumentation connected to the patient.

During an angioplasty or angiographic procedure, a catheter is inserted into a blood vessel of a patient and is used to relieve a constriction due to plaque buildup (an angioplasty procedure) or obtain a visual indication of the condition of the vessel walls (an angiographic procedure). A constriction of the blood vessel or stenosis can occur due to a buildup of plaque within a blood vessel and can be treated in several ways, including drug treatments, thermal treatments, compression treatments utilizing inflatable or expandable devices, etc. all provided to eliminate or reduce the size of the constriction due to plaque buildup. In these procedures it is also desirable or, in many instances necessary, to monitor blood flow and/or pressure during the procedure.

From the above, it is apparent that a definite need in the art exists to eliminate the wiring electrically connecting pressure sensors for pressure sensing related to angioplasty procedures, which are connected to a blood pressure recorder or other equipment.

SUMMARY OF THE INVENTION

The present invention overcomes the deficiencies of the known art and the problems that remain unsolved by providing a method and respective apparatus for wirelessly monitoring blood pressure during an angiographic or angioplasty procedure.

In accordance with one embodiment of the present invention, the invention consists of a disposable manifold assembly for fluid pressure monitoring comprising:

an elongated manifold frame;

a hollow, elongated tubular manifold disposed within the frame and having an inlet end for receiving fluid directly from a patient, an outlet end for returning the fluid to the patient and a passageway extending between the inlet and outlet ends;

at least one valve port and at least one sensing port provided on the tubular manifold intermediate the inlet and outlet ends, each of the at least one valve port and the at least one sensing port being in fluid communication with the passageway and having an opening into the passageway;

a housing formed in the at least one sensing port;

a pressure sensing transducer mounted within the housing, the pressure sensing transducer comprising a sensing surface adapted for direct exposure to fluid flowing through the passageway across the sensing port; and a wireless data transmitter and battery positioned in the housing and in electrical contact with the pressure sensing transducer allowing for wireless transmission of a pressure signal.

In a second aspect, the at least one sensing port is positioned within the elongated manifold frame upstream of the at least on valve port.

In another aspect, the at least one sensing port is positioned adjacent the inlet end.

In yet another aspect, the pressure sensing transducer includes a sensor having a sensing surface and a microchip, the microchip in direct physical contact with the sensor.

In yet another aspect, the microchip is embedded in the sensor.

In yet another aspect, the sensor is formed from a gel material.

In yet another aspect, the sensing surface of the sensor is concave.

In yet another aspect, a back plate is provided and is positioned between the transmitter and the battery.

In yet another aspect, a removable cap is provided and is threaded to the housing and is capable of being loosened and tightened to selectively urge the battery against the transmitter to put the battery and transmitter in electrical contact.

In yet another aspect, the transmitter may be one of a radio frequency or an infrared transmitter.

In yet another aspect, the elongated manifold frame includes a web extending between side walls of the frame and the at least one sensing port extends from the web.

Introducing another embodiment, a system for wirelessly monitoring blood pressure during a medical procedure is provided and includes;

a disposable manifold assembly including:

an elongate hollow manifold having an inlet end, an outlet end and a passageway extending between the inlet end and the outlet end, and a sensing port assembly in fluid communication with the passageway of the manifold, the sensing port assembly including a housing having a pressure sensing transducer and wireless transmitter in direct physical contact with the pressure sensing transducer; and a data receiving and display system including a wireless receiver, a controller in electrical contact with the wireless receiver and a monitor connected to the controller.

In a second aspect, the pressure sensing transducer includes a sensor having a concave sensing surface and a microchip embedded in the sensor.

In another aspect, a batter is positioned within the sensing port assembly and adjacent the transmitter.

In yet another aspect, the data receiving and display system includes a rechargeable battery.

In yet another aspect, the data receiving and display system includes a voltage monitor and alarm connected to the rechargeable battery.

Introducing yet another embodiment, a method of wirelessly monitoring blood pressure within a blood vessel during an angioplasty procedure is provided comprising the steps of:

providing a disposable manifold assembly including:
an elongate hollow manifold having an inlet end, an outlet end and a passageway extending between the inlet end and the outlet end and a sensing port assembly in fluid communication with the passageway of the manifold, the sensing port assembly including a housing having a pressure sensing transducer and a wireless transmitter in direct physical contact with the pressure sensing transducer,
a data receiving and display system including a wireless receiver, a controller in electrical contact with the wireless receiver and a monitor connected to the controller, the wireless receiver being in communication with the wireless transmitter;
an angioplasty catheter having a distal end and a proximal end and defining a guide wire lumen;
advancing the angioplasty catheter through a blood vessel of a patient to a position with the distal end of the angioplasty catheter adjacent a stenosis in the blood vessel;
connecting the proximal end of the angioplasty catheter to the inlet end of the elongated hollow manifold;
flowing blood through the guide wire lumen, into the inlet end of the elongated hollow manifold, and across the pressure sensing port;
sensing pressure exerted by the blood flow with the pressure sensing transducer; and
wirelessly transmitting a signal proportional to the pressure exerted by the blood flow against the pressure sensing transducer from the wireless transmitter to the wireless receiver.

In a second aspect, a portion of the blood flow is captured within a chamber defined between a concave sensing surface of the pressure sensing transducer and the elongated tubular manifold.

In another aspect, the sensing port assembly is positioned within the disposable manifold assembly upstream of any additional port provided in the disposable manifold assembly.

These and other advantages of the invention will be further understood and appreciated by those skilled in the art by reference to the following written specification, claims and appended drawings.

BRIEF DESCRIPTION OF THE DRAWINGS

The invention will now be described, by way of example, with reference to the accompanying drawings, in which.

Like reference numerals refer to like parts throughout the several views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
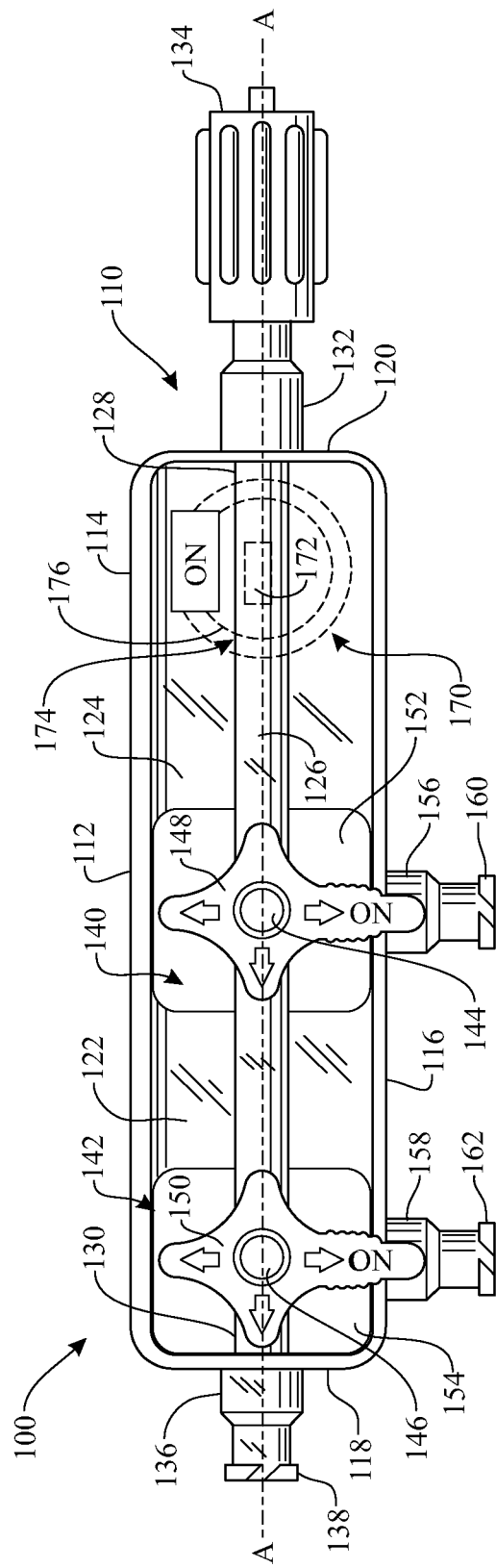
FIG. 1 presents a plan view of a disposable transducer manifold assembly in accordance with the present invention.
Figure 2:
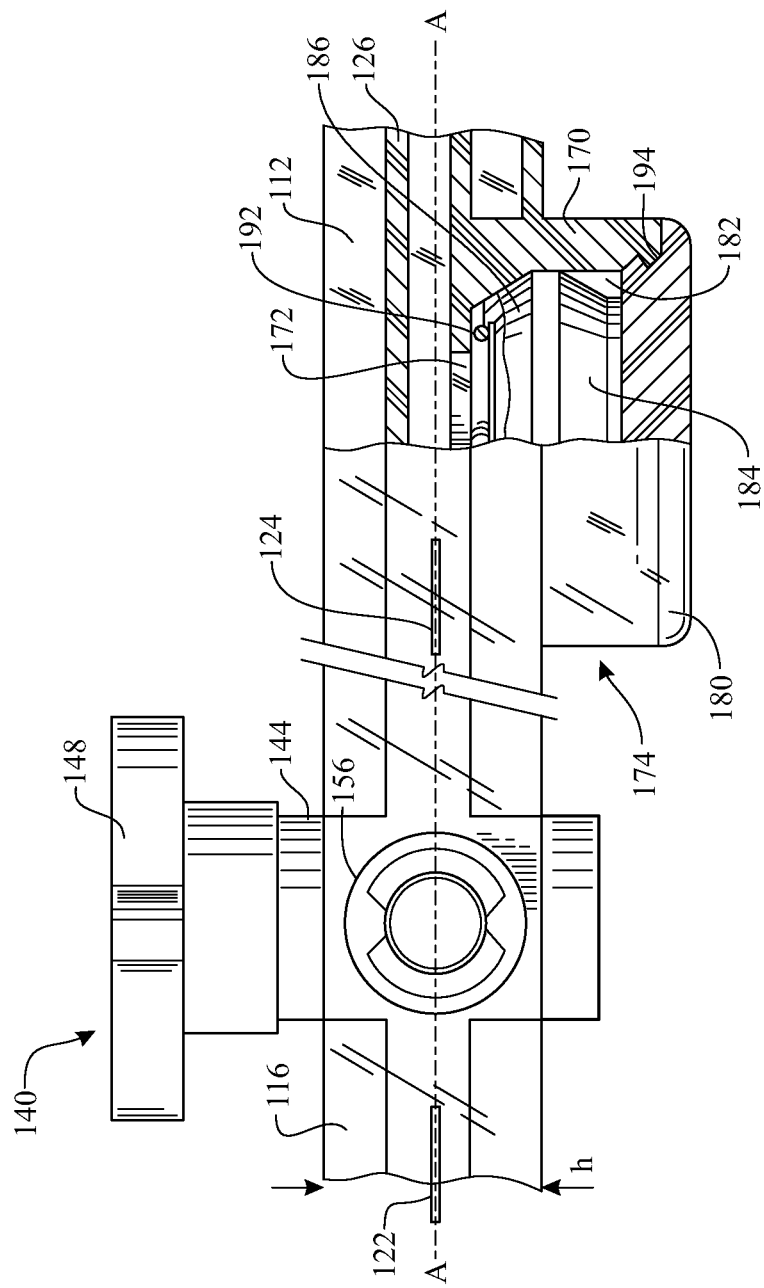
FIG. 2 presents a partial side view of the disposable transducer manifold assembly of FIG. 1, partially sectioned to illustrate the interior of the manifold assembly.
Figure 3:
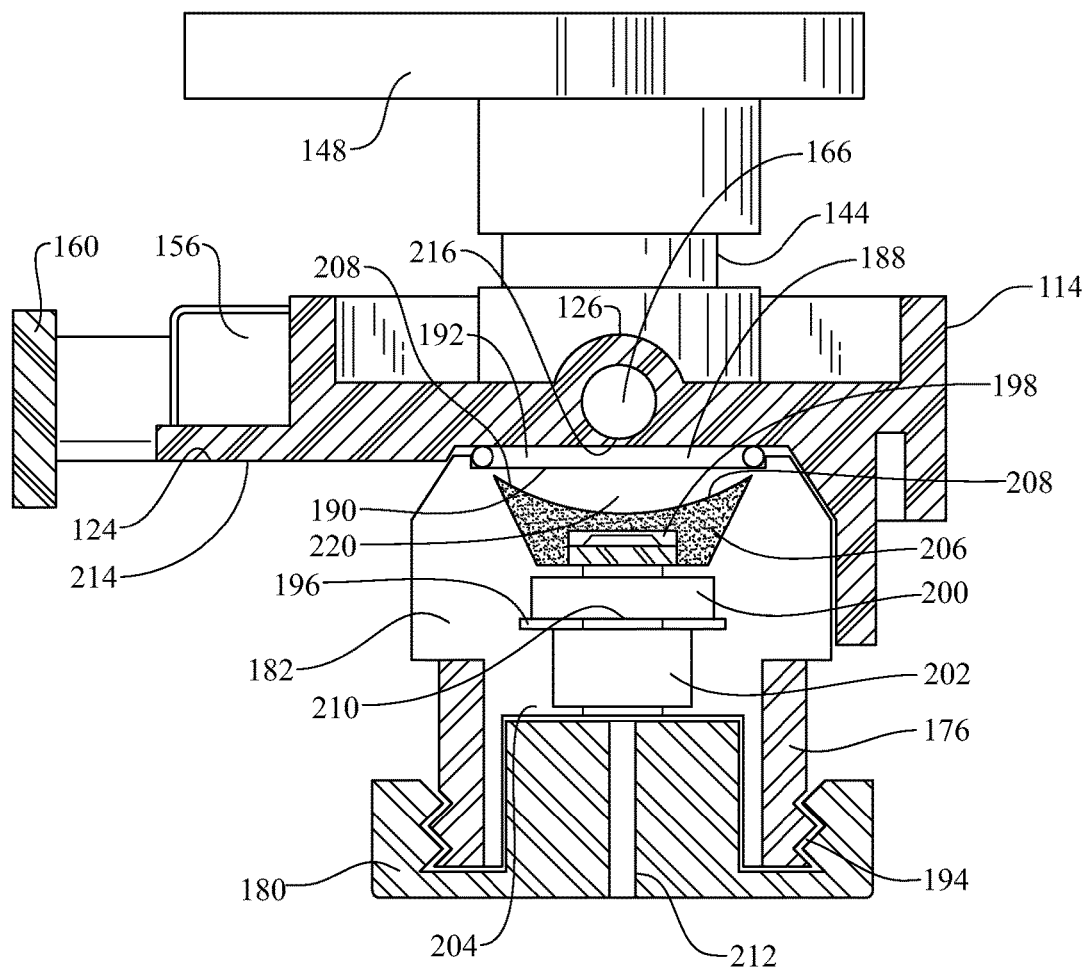
FIG. 3 presents an end view of the disposable transducer manifold assembly illustrated in FIG. 1, also partially sectioned to illustrate the interior of the manifold assembly and the wireless transmission equipment, including a Radio Frequency (RF) or Infra-Red (IR) transmitter, a battery and cap.

With reference to FIGS. 1-3, and initially with regard to FIG. 1, a disposable hydrodynamic transducer manifold assembly or disposable manifold assembly 100 is disclosed for use in monitoring blood pressure or flow in various hemodynamic related procedures, such as, for example, angioplasty or angiographic procedures, etc.

The disposable manifold assembly 100 generally includes a manifold frame 110 comprising a rectangular body portion 112 having a first side wall 114, an opposing second side wall 116, a first end wall 118, and an opposing second end wall 120. A substantially flat left reinforcing spacer wall or web 122 and a substantially flat right reinforcing spacer wall or web 124 extending between the first and second side walls, 114 and 116, at a location substantially midway of the height "h" (see FIG. 2) of the first and second side walls 114 and 116.

In order to allow for blood flow through the disposable manifold assembly 100, a hollow tubular manifold 126 extends from the first end wall 118 to the second end wall 120. A longitudinal axis A-A of the hollow tubular manifold 126 extends substantially coplanar with the reinforcing webs 122 and 124 (see also FIG. 2). The hollow tubular manifold 126 includes a first or inlet end 128 and a second or outlet end 130. A hollow inlet extension 132 is provided on the first end wall 120 of the rectangular body portion 112 of the disposable manifold assembly 100 and is in fluid communication with the inlet end 128 of the hollow tubular manifold 126. The inlet extension 132 includes a slidable coupling member 134 for attachment to a separate catheter (FIG. 5), or the like, to receive blood from a patient (not shown). The disposable manifold assembly 100 additionally includes a hollow outlet extension 136 provided on the second end wall 118 of the rectangular body portion 112 and which is in fluid communication with an outlet end 130 of the hollow tubular manifold 126. The outlet extension 136 includes a flange 138 which may be connected to a return tube (not shown) for further processing of the blood and/or return to the patient. Alternatively, the outlet extension 136 may be capped to prevent blood flow there through, depending on the particular application of the device.

In order to direct blood flow to other monitoring, treatment or return lines, the disposable manifold assembly 100 includes first and second valve port assemblies 140 and 142 in fluid communication with the hollow tubular manifold 126. The first and second valve port assemblies 140 and 142 include respective first and second valve ports 144 and 146, which extend into and through the tubular manifold 126. The first and second valve ports 144 and 146 telescopically receive conventional first and second petcocks 148 and 150, respectively, which contain rotatable valves as are well understood in the art. The first and second valve port assemblies 140 and 142 are supported within the manifold frame 110 by first and second support plates 152 and 154, which are affixed to the manifold frame 110. Alternatively, the first and second support plates 152 and 154 may be integrally formed with the manifold frame 110.

The first and second valve port assemblies 140 and 142 additionally include respective first and second outlet ports 156 and 158. The first and second outlet ports 156 and 158 are integrally joined to the first and second valve ports 144 and 146, such that each petcock 148, 150 can direct blood from the hollow tubular manifold 126 through the respective first outlet port 156 or the second outlet port 158. Alternatively, when rotated, the first and second petcocks 148, 150 can direct fluid through both the outlet ports 156, 158 and the hollow tubular manifold outlet extension 136 simultaneously. Further, the first and second petcocks 148, 150 can be rotated to bypass the respective first and second outlet ports 156, 158 and direct the blood flow directly through the hollow tubular manifold 126 and out the outlet extension 136, in a manner well understood by those skilled in the art.

The first and second outlet ports 156, 158 are formed with enlarged respective first and second coupling portions 160, 162, which are adapted to receive flexible plastic tubes which carry blood from the manifold to a hemodynamic recorder, or sensing/monitoring or other treatment stations or equipment.

While the disposable manifold assembly 100 is disclosed with two outlet ports, 156, 158, it is contemplated that more or less outlet ports may be provided.

In this embodiment, all elements described hereinabove with the exception of the slidable coupling member 134 and the first and second petcocks 148, 150 can be formed as an integral molded unit, preferably constructed of a transparent polycarbonate plastic material.

As best shown in FIG. 1, the left web 122 is located between the first and second valve port assemblies 140, 142. The left web 122 supports the hollow tubular manifold 126 between the first and second valve port assembles 140, 142 to prevent twisting of the hollow tubular manifold 126 during operation of the first and second petcocks 148, 150.

As further shown, the right web 124 is extends between the first valve port assembly 140 and the second end wall 120 of the manifold frame 110.

Referring now to FIGS. 1 and 2, in order to measure blood pressure and flow of a patient, the disposable manifold assembly 100 additionally includes a sensing port assembly 170 in fluid communication with the hollow tubular manifold 126 through a rectangular aperture 172 formed through the hollow tubular manifold 126. The sensing port assembly 170 includes a first housing portion 174, which surrounds the rectangular aperture 172 in the hollow tubular manifold 126 and is also integrally molded to the frame. Specifically, the first housing portion 174 includes a substantially annular wall 176, which joins the manifold frame 110 and is supported on the undersurface 214 (FIGS. 2 and 3) of the right web 124

Referring now to FIG. 2, a lower cap portion 180 is provided and may be snapped or otherwise fastened to the annular wall 176 so that a substantially hollow chamber 182 is formed.

A pressure sensing transducer 184 is enclosed within the hollow chamber 182. In this exemplary embodiment, the pressure sensing transducer 184 is preferably a microchip pressure sensor, which has an on-chip automatic temperature compensation and calibration circuit, though the sensor is not limited to this particular design. The pressure sensing transducer 184 includes a thermoplastic case 186 having a counter bore 188 which forms a flat surface 190 on which rests an O-ring 192. The O-ring 192 seals the pressure sensing transducer 184 against the hollow tubular manifold 126. Threads 194 are employed to retain the lower cap portion 180 to the first housing portion 174 and seal the pressure sensing transducer 184 within the hollow chamber 192.

Referring now to FIG. 3, in order to eliminate the typical cables connecting the pressure sensing transducer 184 to an external or remote monitoring system (not shown), the sensing port assembly 170 further includes a metal back plate 196, microchip 198, Radio Frequency (RF) or Infrared (IR) transmitter 200 and battery 202. The threads 194 on the lower cap portion 180 allow the transmitter 200 to be selectively electrically coupled to the battery 202, depending whether the lower cap portion 180 is tightened, or loosened, thus allowing the lower cap portion 180 to act as a switch. Specifically, an inner portion 204 of the lower cap portion 180 is in direct contact with the battery 202. The microchip 198 is itself enclosed within a gel 206 formed with a concave sensing surface 208.

The microchip 198 is supported on a circuit board (not shown), which, in turn, is supported on the metal back plate 196, which is permanently secured within the thermoplastic case 186. An aperture 210 is formed within the metal back plate 196 and an aligned aperture 212 is formed in the thermoplastic case 186 to vent the interior of the pressure sensing transducer 184 to atmosphere. Specifically, the aperture 212 is formed through the lower cap portion 180.

In one embodiment, the radio frequency (RF) or infrared (IR) transmitter 200 is a 2.4 GHz model such as, for example, a 2.4 GHz transmitter manufactured by Anaren Integrated Radio or "AIR" transmitter for short. This transmitter is designed for license free Industrial, Scientific and Medical ("ISU") uses. Alternatively, a 915 MHz can be used to extend a signal range. The battery 202 can be a coin type battery such as a CR-2016 manufactured by Panasonic. The microchip 198 can be a MPX 2010D OR MPX 2050D.

It should be noted that the first housing portion 174 of the sensing port assembly 170 is formed of a material that is transparent to radio frequency (RF) and/or infrared (IR) waves.

It will be understood that other suitable pressure sensing transducers may be utilized in conjunction with the invention. For example, in a similar transducer to that described herein, it is possible to employ a diaphragm in place of the gel 206 to act as the pressure-sensing surface.

It should be noted that the sensing port assembly 170 is located within the manifold frame 110 adjacent the inlet end 128 and upstream of the first and second valve port assemblies 140 and 142. This allows the sensing port assembly 170 to get a more accurate reading of sensed blood pressure or flow without turbulent interference from the first and second valve port assemblies 140 and 142.

It should be further noted that the radio frequency (RF) or infrared (IR) transmitter 200 is not only contained entirely within the disposable manifold assembly 100 but is also fully contained and/or embedded within the hollow chamber 182 of the sensing port assembly 170.

To assemble the sensing port assembly 170, the pressure sensing transducer 184 is positioned within the hollow chamber 182 of the first housing portion 174. The lower cap portion 180 is threaded onto the first housing portion 174. This causes the pressure sensing transducer 184 to be pressed into engagement with the under surface 214 of the right web 124 in surrounding relationship to an aperture 216 formed in the hollow tubular manifold 126 as illustrated in FIG. 3. It will thus be appreciated that the concave sensing surface 208 is exposed directly to blood in the hollow tubular manifold 126 via the aperture 216. At the same time, the O-ring 192 prevents the escape of fluid past the pressure sensing assembly 179 and out of the disposable manifold assembly 100.

In use, the above-described disposable transducer manifold assembly 100 may be utilized in a continuous blood pressure sensing and monitoring process. The hollow tubular manifold 126 is provided having an inlet at one end and at least one sensing port assembly 170. The pressure sensing transducer 184 is secured directly to the hollow tubular manifold 126 such that the concave sensing surface 208 of the pressure sensing transducer 184 is exposed directly to blood in the hollow tubular manifold 126 through the sensing port assembly 170. The concave sensing surface 208 is sealed relative to the sensing port assembly 179 through the use of the O-ring 192.

Next the RF or IR transmitter 200 is installed. After this the battery 202 is installed in a proper orientation. When it is desired to transmit pressure signals from the RF or IR transmitter 200, the lower cap portion 180 is tightened on the threads 194 to put the battery 202 in contact with the RF or IR transmitter 200. When the disposable manifold assembly 100 is not in use, the lower cap portion 180 is loosened on the threads 194 to electrically disconnect or isolate the battery 202 from the RF or IR transmitter 200.

Figure 4:
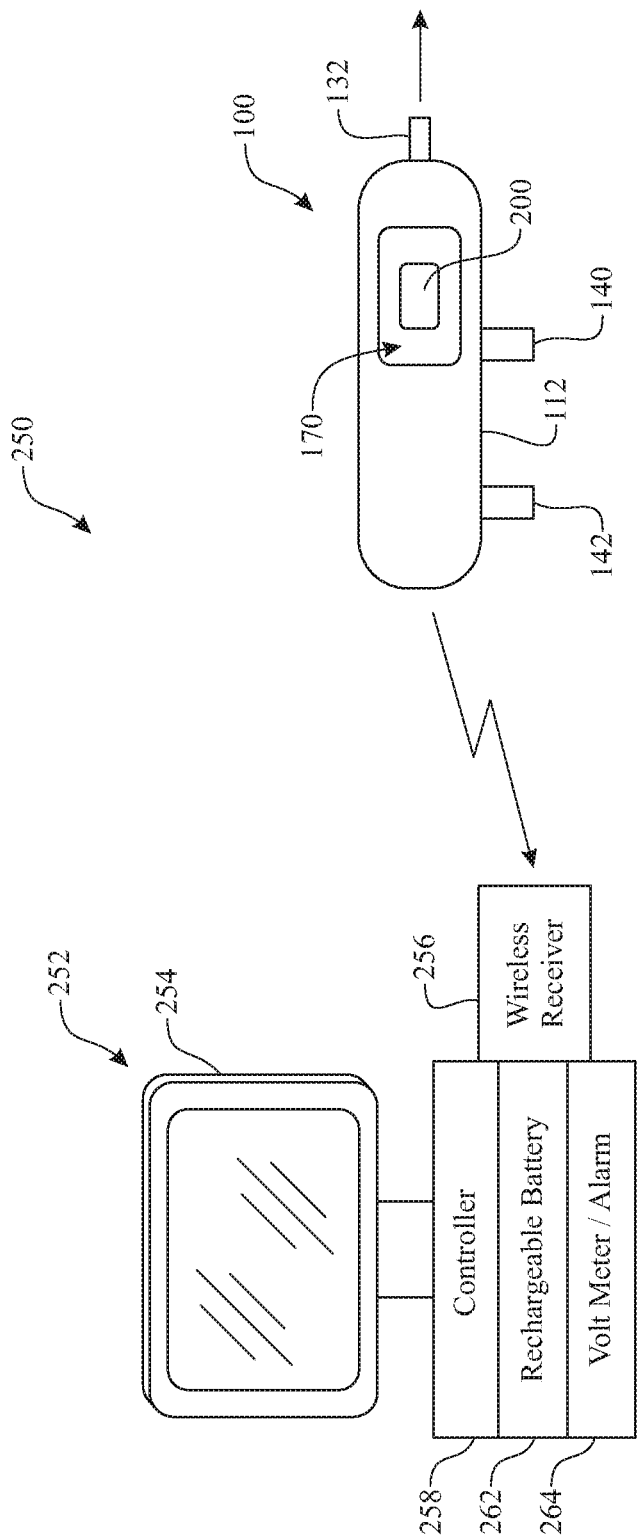
FIG. 4 presents a schematic view of an exemplary wireless blood pressure monitoring system incorporating the disposable transducer manifold assembly of FIG. 1.

Referring now to FIG. 4, the disposable manifold assembly 100 incorporating sensing port assembly 170 may be incorporated into a wireless blood pressure monitoring system 250 including a data receiving and display assembly 252 having a monitor 254, a wireless receiver 256 and a controller 258. The controller 258 is provided to receive data from the sensing port assembly 170, through the wireless receiver 256, and present it on the monitor 254 for viewing by medical personal. The monitor 254 can be of any know type such as, for example, video screen, liquid crystal display screen, etc. In a preferred embodiment, the monitor is a plasma screen.

The monitor 254, the controller 258 and the wireless receiver 256 may be powered by any conventional power outlet, such as a 110 Volt alternating current source, or as in a preferred embodiment, can be powered by a portable power supply such as a rechargeable battery 262, a solar power converter, and the like. A voltage monitor and alarm 264 may be connected to the rechargeable battery 262 to ensure the power level does not drop below a predetermined threshold and if the power does drop below the predetermined threshold, notify the operator via the included alarm circuitry.

Figure 5:
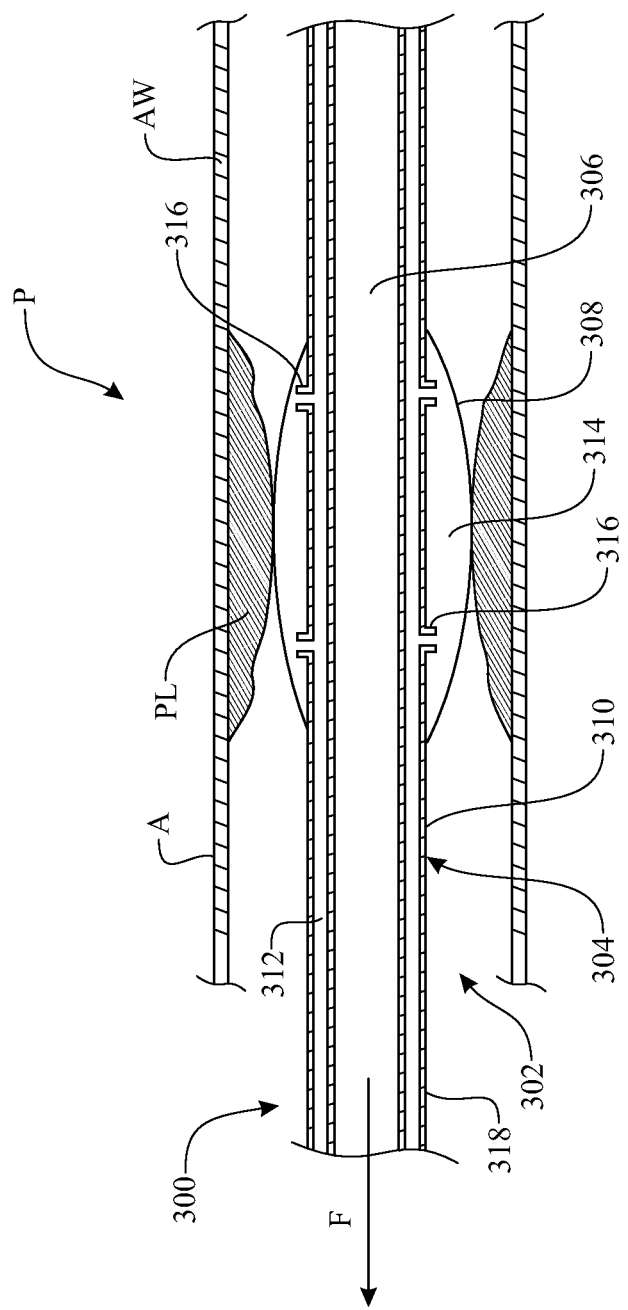
FIG. 5 presents a sectioned side view of an exemplary balloon angioplasty catheter positioned within a blood vessel at a stenotic site.

Referring now to FIG. 5, the disclosed wireless blood pressure monitoring system 250 may be connected to an angioplasty catheter 300 for use in obtaining blood pressure readings wirelessly during an angioplasty or angiographic procedure. When used in a balloon angioplasty procedure, the angioplasty catheter 300 is in the form of a balloon angioplasty catheter 302 having a hollow catheter tube 304 defining a guide wire lumen 306 and an inflatable balloon 308 secured to an outer surface 310 of the hollow catheter tube 304. The hollow catheter tube 304 additionally includes an inflation lumen 312 in fluid communication with an interior 314 of the inflatable balloon 308 through one or more inflation ports 316 extending through the hollow catheter tube.

Referring to FIGS. 3, 4, and 5, and the use of the disposable manifold assembly 100 in conjunction with the data receiving and display assembly 252 and the balloon angioplasty catheter 302 in a balloon angioplasty procedure to relieve a stenosis in a blood vessel will now be described. Initially, with regard to FIGS. 4 and 5, a fully charged battery 262 is installed in the data receiving and display assembly 252 and the sensing port assembly 170 of the disposable manifold assembly 100 is assembled as described hereinabove. Alternatively, the disposable manifold assembly 100 may be packaged with the sensing port assembly 170 preassembled requiring only the removal of a card or plastic spacer (not shown) to expose the transmitter 200 to the battery 202 (FIG. 3). A proximal end 318 of the hollow catheter tube 304 is connected to the inlet extension 132 of the disposable manifold assembly 100. The wireless blood pressure monitoring system 250 along with the balloon angioplasty catheter 302 are thus prepared for use in a balloon angioplasty procedure.

With specific reference to FIG. 5, the balloon angioplasty catheter 302 is inserted into an artery A of a patient P by accessing the artery A in known manner and inserting a guide wire (not shown) through artery A and past an area of plaque PL build up. Thereafter, the balloon angioplasty catheter 302 is advanced over the guide wire until the balloon 308 of the balloon angioplasty catheter 302 is positioned adjacent the plaque P. The guide wire can then be removed. At this point, the balloon 308 is in a deflated state and blood may still flow somewhat freely past the balloon angioplasty catheter 302.

Referring now to FIGS. 3 and 4, to prepare the wireless blood pressure monitoring system 250 for use, the lower cap portion 180 is turned or screwed in on the threads 194 to urge the battery 202 against the transmitter 200 to turn on or "power up" the sensing port assembly 170 of the disposable manifold assembly 100 for use in wirelessly transmitting blood pressure readings to the data receiving and display assembly 252. Similarly, the controller 258 of the data receiving and display assembly 252 is turned on to power up the wireless receiver 256, the controller 258, the monitor 254 and the voltage monitor/alarm 264 from the rechargeable battery 262. In this manner, the data receiving and display assembly 252 is wirelessly connected to the disposable manifold assembly 100 and, more specifically, to the sensing port 170 for receipt of blood pressure readings.

Referring to FIG. 5, once the wireless blood pressure monitoring system 250 has been powered up, a fluid (not show) such as, for example, saline, carbon dioxide or other biocompatible fluid is passed through the inflation lumen 312 of the balloon angioplasty catheter 302 and into the interior 314 of the balloon 308 to inflate the balloon 308. Inflation of the balloon 308 compresses the plaque PL back against the arterial wall AW to relieve the stenotic constriction. Blood flow around the balloon angioplasty catheter 302 is cut off and the blood flow F now passes through the guide wire lumen 306 of the balloon angioplasty catheter 302 and back through the inlet extension 132 on the disposable manifold assembly 100.

With reference specifically to FIG. 3, blood flowing into and through the inlet extension 132 passes into a passageway or interior 166 of the hollow tubular manifold 126. A small portion of the blood passes through the aperture 216 and into a sensing chamber 220 formed between the hollow tubular manifold 126 and the concave sensing surface 208 of gel 206.

The pressure exerted by the blood on the concave sensing surface 208 is transmitted against the pressure sensing transducer 184, specifically the microchip 198, which converts the pressure force to an electrical pulse or signal. This electrical signal is conveyed to the transmitter 200, which then wirelessly transmits the signal to the data receiving and display system 252. As discussed hereinabove, the positioning or embedding of the transmitter 200 directly within the sensing port assembly 170 provides a compact device capable of a high degree of accuracy. The accuracy is further enhanced by positioning the sensing port assembly 170 immediately adjacent the inlet extension 132 and upstream from any remaining ports thereby avoiding turbulent interference with the blood flow.

Referring to FIG. 4, the wireless signal transmitted from the transmitter 200 of the disposable manifold assembly 100 is received by the wireless receiver 256 of the data receiving and display assembly 252 and converted into a data source by the controller 258 for display on the monitor 254. It should be noted that, should the power level of the rechargeable battery 262 fall below a predetermined threshold, the level will be detected by the voltage meter/alarm 264 and a visual and/or audible signal will be provided to alert the doctor, surgeon or staff.

It should be noted that, in some surgical procedures, it may be desirable to position and inflate the balloon 308 prior to connecting the balloon angioplasty catheter 302 to the disposable manifold assembly 100 and/or "powering up" the sensing port assembly 170 or the data receiving and display assembly 252.

Thus, in this manner, the disposable manifold assembly 100, incorporating the sensing port assembly 170 wirelessly transmits blood pressure readings to the data receiving and display assembly 252 without the use of cable or wires. The lack of cables and/or wires greatly increases safety within the operative theater and also increases the options of locating the position of the monitor 254 for viewing by a doctor or surgeon.

While the preferred embodiments of the invention have been described above, it will be recognized and understood that various modifications can be made in the invention and the appended claims are intended to cover all such modifications which may fall within the spirit and scope of the invention.

What is claimed is:

1. A disposable manifold assembly for fluid pressure monitoring comprising:
   an elongated manifold frame;
   a hollow, elongated tubular manifold disposed within said frame and having an inlet end for receiving fluid directly from a patient, an outlet end for returning said fluid to said patient and a passageway extending between said inlet and outlet ends;
   at least one valve port and at least one sensing port provided on said tubular manifold intermediate said inlet and outlet ends, each of said at least one valve port and said at least one sensing port being in fluid communication with said passageway and having an opening into said passageway;
   a housing formed in said at least one sensing port;
   a pressure sensing transducer mounted within said housing, said pressure sensing transducer comprising a sensing surface adapted for direct exposure to fluid flowing through said passageway across said at least one sensing port;
   a wireless data transmitter and battery positioned in said housing and in electrical contact with the pressure sensing transducer allowing for wireless transmission of a pressure signal;
   a back plate positioned in said housing;
   a removable cap attachable to said housing, said removable cap being adjustable to selectively urge said battery to create an electrical connection between said battery and said wireless data transmitter;
   wherein to measure blood pressure of said patient, the at least one sensing port is in fluid communication with the tubular manifold through an aperture formed through the tubular manifold;
   wherein the housing formed in said at least one sensing port surrounds the aperture in the tubular manifold and is integrally molded to the manifold frame;
   wherein the housing formed in said at least one sensing port includes a substantially annular wall which joins the manifold frame and is supported on a surface of the manifold frame;
   wherein the removable cap is attachable to the annular wall of the housing such that a substantially hollow chamber is formed in the housing formed in said at least one sensing port;
   wherein the pressure sensing transducer is enclosed within the substantially hollow chamber in the housing formed in said at least one sensing port;
   wherein threads retain the removable cap to the housing and seal the pressure sensing transducer within the substantially hollow chamber in the housing;
   to assemble the at least one sensing port, the pressure sensing transducer is positioned within the substantially hollow chamber of the housing and the removable cap is threaded onto the housing; and
   wherein the pressure sensing transducer is located directly adjacent to the wireless data transmitter and the wireless data transmitter is directly adjacent to the back plate such that said wireless data transmitter is in direct physical contact with said pressure sensing transducer.

2. The disposable manifold assembly as recited in claim 1, wherein said at least one sensing port is positioned within said elongated manifold frame upstream of said at least on valve port.

3. The disposable manifold assembly as recited in claim 2, wherein said at least one sensing port is positioned adjacent said inlet end.

4. The disposable manifold assembly as recited in claim 1, wherein said pressure sensing transducer includes a microchip.

5. The disposable manifold assembly as recited in claim 4, wherein said microchip is embedded in said pressure sensing transducer.

6. The disposable manifold as recited in claim 5, wherein said microchip is enclosed within a gel.

7. The disposable manifold as recited in claim 5, wherein said sensing surface is concave.

8. The disposable manifold assembly as recited in claim 1, wherein the back plate comprises a metal back plate permanently secured and positioned between said wireless data transmitter and said battery, the metal back plate having an aperture formed within the metal back plate and aligned with an aperture formed through the removable cap to vent an interior of the pressure sensing transducer.

9. The disposable manifold assembly as recited in claim 1, wherein said wireless data transmitter is at least one of a radio frequency (RF) transmitter and an infrared (IR) transmitter.

10. The disposable manifold assembly as recited in claim 1, said elongated manifold frame further comprising a web extending between side walls of said frame, wherein said at least one sensing port extends from said web.

* * * * *